(12) United States Patent
Havard

(10) Patent No.: US 11,167,106 B2
(45) Date of Patent: Nov. 9, 2021

(54) CATHETER

(71) Applicant: The Flume Catheter Company Limited, Suffolk (GB)

(72) Inventor: John Spencer Havard, Suffolk (GB)

(73) Assignee: The Flume Catheter Company Limited, Suffolk (GB)

(*) Notice: Subject to any disclaimer, the term of this patent is extended or adjusted under 35 U.S.C. 154(b) by 364 days.

(21) Appl. No.: 16/252,598

(22) Filed: Jan. 19, 2019

(65) Prior Publication Data

US 2019/0151609 A1 May 23, 2019

Related U.S. Application Data

(63) Continuation of application No. 14/915,378, filed as application No. PCT/GB2014/052588 on Aug. 26, 2014, now Pat. No. 10,195,394.

(30) Foreign Application Priority Data

Aug. 27, 2013 (GB) ..................................... 1315227
Jan. 29, 2014 (GB) ..................................... 1401538

(51) Int. Cl.
*A61M 25/00* (2006.01)
*A61M 25/04* (2006.01)
*A61M 25/10* (2013.01)

(52) U.S. Cl.
CPC ...... *A61M 25/0017* (2013.01); *A61M 25/007* (2013.01); *A61M 25/04* (2013.01);
(Continued)

(58) Field of Classification Search
CPC ............ A61M 25/0017; A61M 25/007; A61M 25/1002; A61M 2025/1004; A61M 2025/1086; A61M 2025/1065
See application file for complete search history.

(56) References Cited

U.S. PATENT DOCUMENTS 3,811,448 A 5/1974 Morton
3,889,686 A 6/1975 Duturbure
(Continued)

FOREIGN PATENT DOCUMENTS

CN 202020780 U 11/2011
CN 102380154 A 3/2012
(Continued)

*Primary Examiner* — Susan S Su
(74) *Attorney, Agent, or Firm* — Potomac Law Group, PLLC; Vincent M DeLuca

(57) ABSTRACT

A catheter has an elongate shaft with a longitudinal drainage bore for conveying fluid along the shaft. An elongate, tapered tip portion extends from an end of the shaft, the tip portion having a distal end furthest from the shaft, and a drainage aperture is provided in the tip portion, being in fluid communication with the bore. An inflatable balloon element is attached to the tip portion. The balloon element is configured such that when it is fully inflated, at least a portion of the balloon element extends around the distal end of the tip portion and extends along the tip portion to a point on an opposite side of the drainage aperture to the distal end, a surface of the balloon element including a depression providing a passageway in fluid communication with the drainage aperture.

10 Claims, 5 Drawing Sheets

(52) U.S. Cl.
CPC . *A61M 25/1002* (2013.01); *A61M 2025/0019* (2013.01); *A61M 2025/107* (2013.01); *A61M 2025/1093* (2013.01)

(56) References Cited

U.S. PATENT DOCUMENTS

| | | |
|---|---|---|
| 3,954,110 A | 5/1976 | Hutchison |
| 4,351,342 A | 9/1982 | Wiita et al. |
| 5,250,029 A | 10/1993 | Lin et al. |
| 2002/0173816 A1 | 11/2002 | Hung |
| 2006/0167406 A1 | 7/2006 | Quinn |
| 2008/0071250 A1 | 3/2008 | Crisp |
| 2009/0221992 A1 | 9/2009 | Hannon et al. |
| 2010/0234668 A1 | 9/2010 | Roeder et al. |
| 2011/0190737 A1 | 8/2011 | Rocco |
| 2012/0203210 A1 | 8/2012 | Schanz et al. |
| 2013/0281926 A1 | 10/2013 | Raux et al. |
| 2015/0359996 A1 | 12/2015 | Arora et al. |
| 2020/0384242 A1 * | 12/2020 | Havard ............... A61M 25/007 |

FOREIGN PATENT DOCUMENTS

| | | |
|---|---|---|
| NL | 8303510 A | 5/1985 |
| WO | 92/00117 A1 | 1/1992 |
| WO | 2007/005734 A2 | 1/2007 |
| WO | 2010/090671 A1 | 8/2010 |

\* cited by examiner

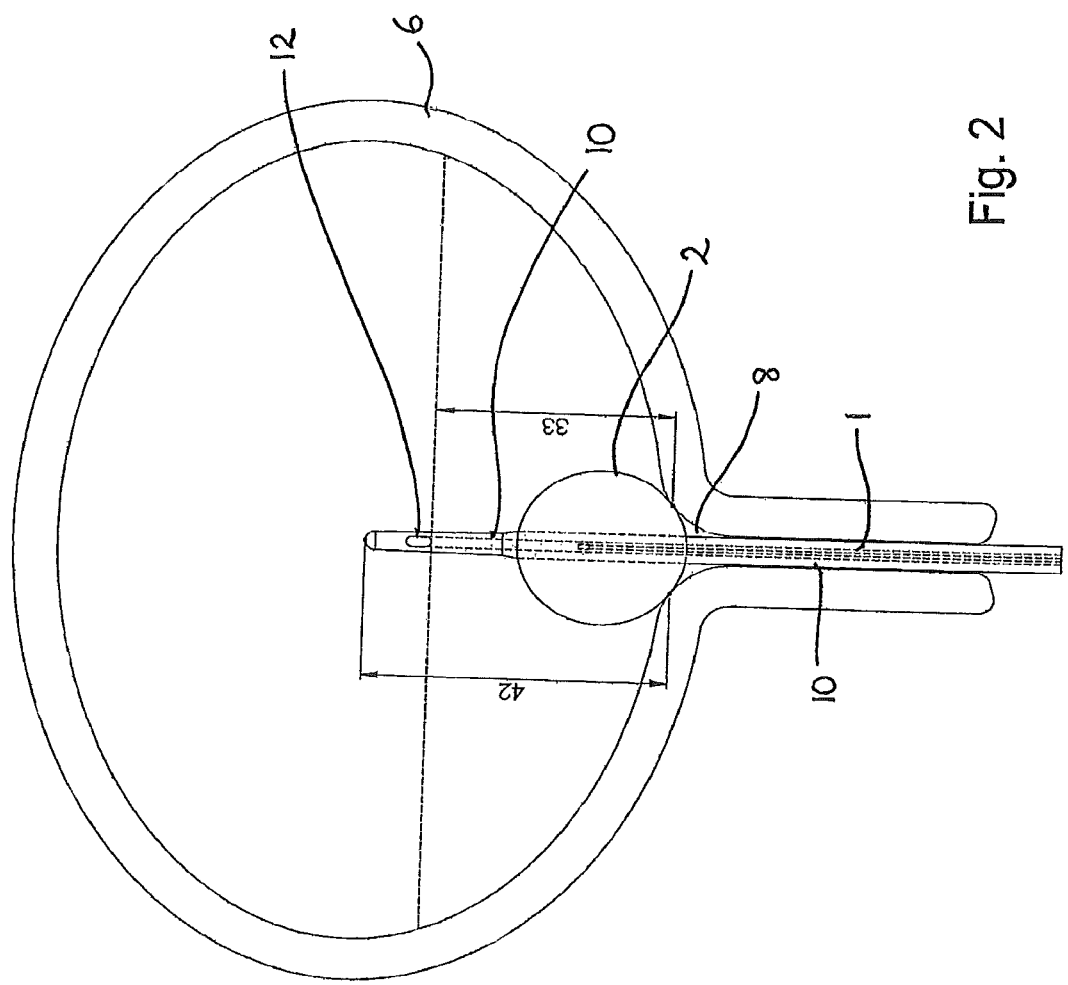

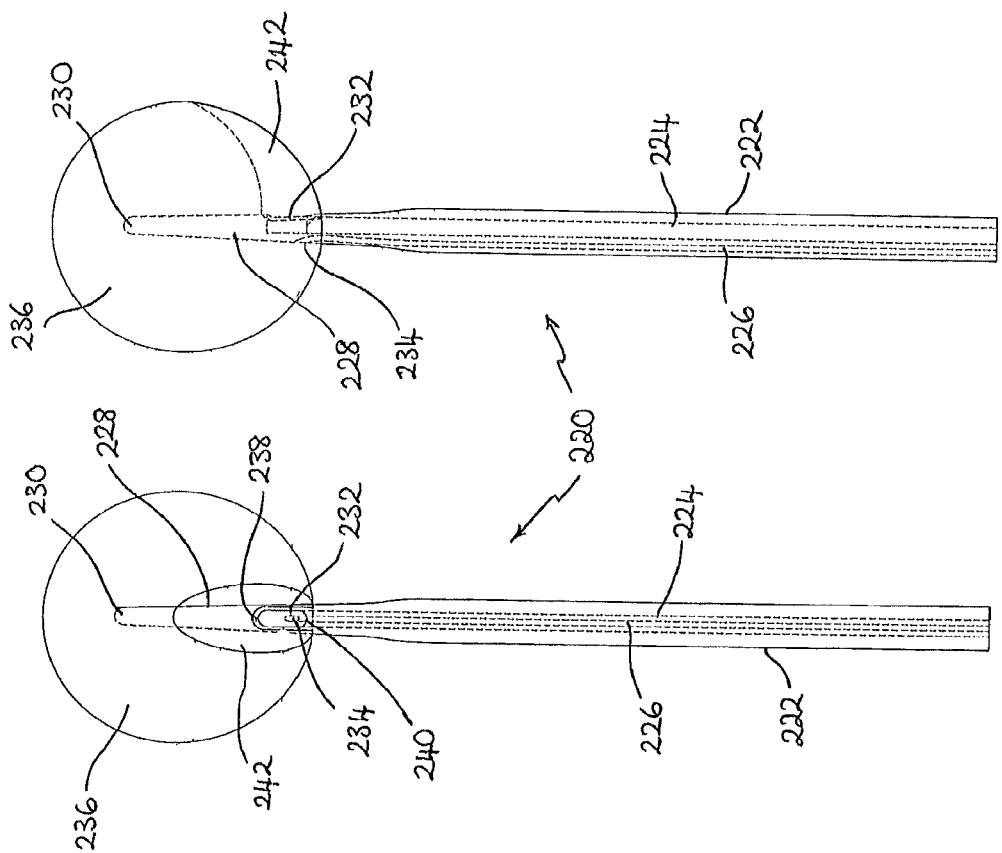
Fig. 4
Fig. 5
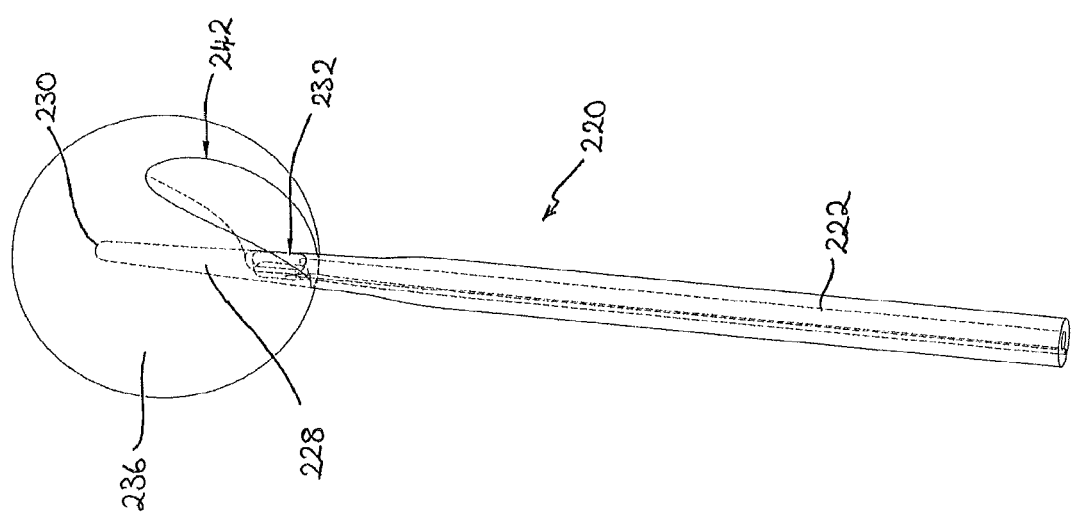
Fig. 3

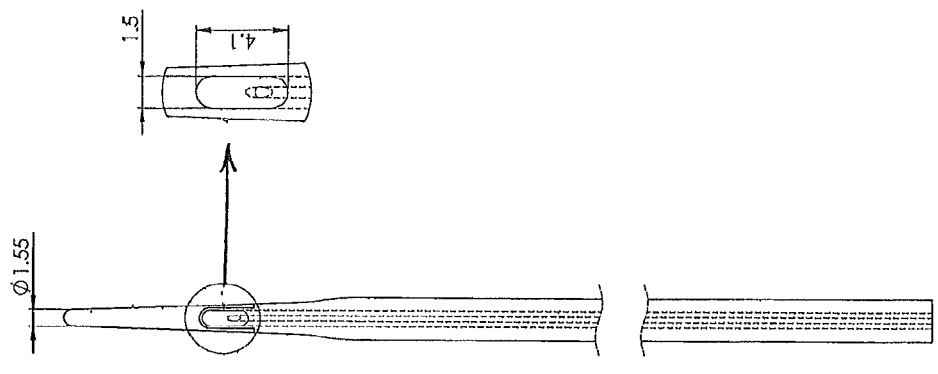
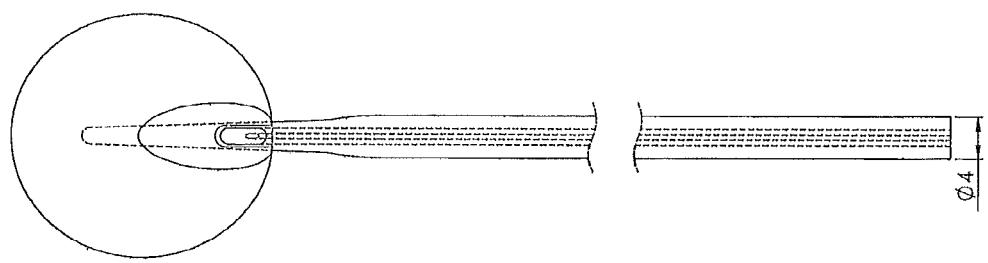
Fig. 7
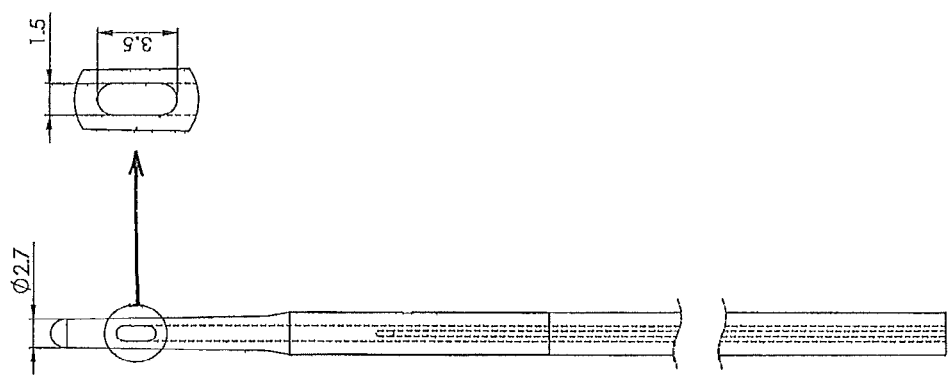
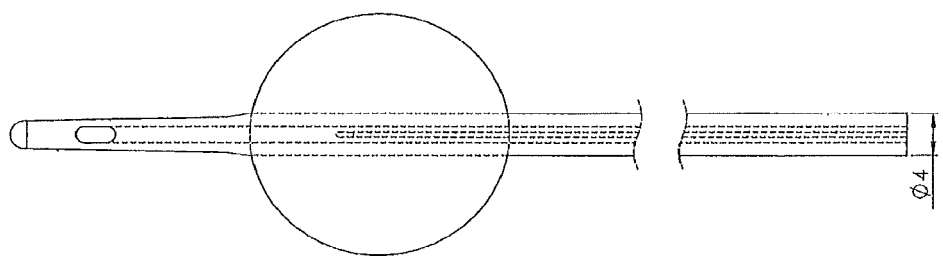
Fig. 6

CATHETER

BACKGROUND a. Field of the Invention

This invention relates to a catheter, and in particular to a urinary catheter.

b. Related Art

Current catheters have an inflatable balloon to keep the catheter in situ in the bladder and urine drainage apertures above the balloon and below the tip of the catheter.

This means there remains residual urine in the bladder below the level of the drainage holes. This urine tends to become infected and, through well understood processes, cause encrustations and catheter blockage. This in turn leads to patient discomfort and bypassing of urine that then demands an urgent change of catheter when the whole process only starts again. Some patients with chronic conditions have catheters that may only last a couple of weeks so over the years these individuals have to sustain a lot of discomfort with recurrent blockages and changes. The National Health Service (NHS) in the United Kingdom or funding authorities over the world have to fund catheter changes that often occur as emergencies when the costs are high. The clinical and financial problem is massive since there are currently 100 million catheters in use.

Another disadvantages of current catheter designs include damage or trauma to the bladder wall by the catheter tip, and damage to the bladder wall due to the bladder wall being sucked into the drainage hole, caused by the dome of the bladder collapsing over the drainage hole.

It is, therefore, an object of the present invention to provide an improved catheter that overcomes at least some of the problems associated with prior art catheters.

SUMMARY OF THE INVENTION

According to the present invention, there is provided a catheter comprising:
  an elongate shaft having a longitudinal drainage bore for conveying fluid along the shaft;
  an elongate, tapered tip portion extending from an end of the shaft, the tip portion having a distal end furthest from the shaft;
  a drainage aperture provided in the tip portion, said aperture being in fluid communication with said bore, and a length of the tip portion between the drainage aperture and the distal end being at least two times the length of the drainage aperture in the longitudinal direction; and
  an inflatable balloon element attached to said tip portion, the balloon element being configured such that, when fully inflated, the balloon element is substantially spherical and fully surrounds the distal end of the tip portion and extends along the tip portion to a point on an opposite side of the drainage aperture to said distal end, a surface of the balloon element including a depression providing a passageway in fluid communication with the drainage aperture,
  wherein, when the balloon element is inflated, the depression in the surface of the balloon element does not extend beyond the distal end of the tip portion.

The catheter will typically be a urethral catheter.

Preferably the catheter further comprises:
  an inflation bore provided in the shaft; and
  an inflation aperture provided in the tip portion, the inflation aperture being in fluid communication with the inflation bore and with an internal volume of the balloon element.

Preferably the inflation aperture is provided on an opposite side of the tip portion to the drainage aperture.

Preferably a dimension of the balloon element, when fully inflated, in a longitudinal direction is at least three times the dimension of the drainage aperture in the longitudinal direction.

The catheter design of the present invention, therefore, allows complete emptying of the bladder which will tackle the main factor influencing blockage. The balloon will retain the catheter in the bladder and the design has a missing half segment at the bottom where the drainage aperture is located. This allows complete bladder drainage while ensuring the aperture remains positioned at the base of the bladder. Since the hole is at the level of the balloon and not above it this means the length of catheter above the balloon can be shortened. This fact, combined with the inflatable tip, will both reduce trauma from the catheter tip to the bladder and also eliminate bladder wall damage from being sucked into the drainage hole. Catheter life, damage to the bladder wall and insertion difficulties will all be greatly improved with the catheter of the present invention.

BRIEF DESCRIPTION OF THE DRAWINGS

The invention will now be further described, by way of example only and with reference to the accompanying drawings, in which:
FIG. 2 shows an example of a know, prior art catheter in position within a bladder;
FIG. 3 shows a catheter according to a preferred embodiment of the present invention;
FIG. 4 is a plan view from the front of the catheter of FIG. 3;
FIG. 5 is a plan view from the side of the catheter of FIG. 3;
FIG. 6 illustrates an example of a known, prior art catheter;
FIG. 7 illustrates an embodiment of a catheter of the present invention.

DETAILED DESCRIPTION

Figure 1:
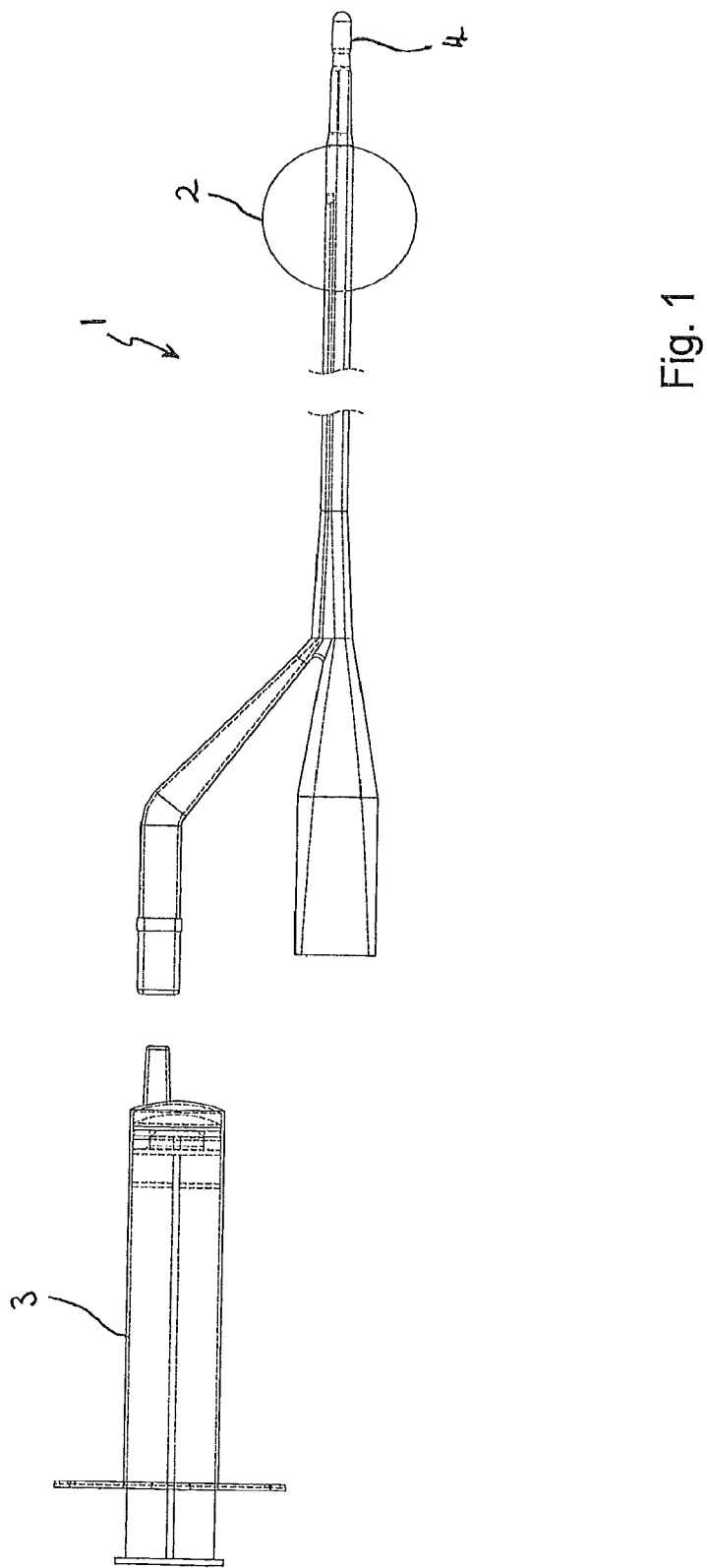
FIG. 1 shows an example of a known, prior art catheter.

As shown in FIG. 1, it is known to provide catheters 1 with retention balloons 2 that function to retain the distal end 4 of the catheter 1 within a bladder during use. The catheters 1 may be supplied with a pre-filled water balloon or may use a syringe 3 to inflate the distal retention balloon. They are also made of differing materials but the spherical retention balloon 2 is a common feature to them all.

FIG. 2 illustrates a prior art catheter 1 inserted and functioning within a bladder 6. The balloon 2 sits over the urethral exit 8 from the bladder 6 and seals it along with the catheter tubing 10 itself. The drawing demonstrates that the bladder 6 can never empty because the drainage hole 12 sits approximately 33 mm into the bladder 6. This is the fundamental design flaw of current catheters, because stagnant urine remaining in the bladder encourages infection, commonly by *Proteus Mirabilis*. This then leads to the sequence of biofilm formation followed by crystal deposition in the urine carrying tubing 10 called encrustation, which then causes catheter blockage. The other feature of this drawing is that it clearly shows 42 mm of tubing 10 inside the bladder 6. The tip 14 of the catheter 1 has been shown to cause bladder damage but also the bladder wall can be sucked into the drainage hole 12. The bladder 6 tends to collapse from the top hence it is possible for the walls to get damaged in this way.

FIGS. 3 to 5 illustrate a preferred embodiment of a catheter 220 according to the present invention. The catheter 220 comprises an elongate shaft 222 having two bores 224, 226 extending axially along its length. The bores 224, 226 allow fluids, in particular water and urine, to travel through the shaft 222. In particular, a first bore 224 is a drainage bore 224 and a second bore 226 is an inflation bore. At an end of the shaft 222 is a tapered tip portion 228. The tip portion 228 is elongate and extends coaxially from the end of the shaft 222, terminating at a distal end 230 of the catheter 220.

This is the only urethral catheter design that has a graduated or tapered profile of the tip 228 to allow gentle urethral dilatation during insertion which should therefore be easier to execute. The distal end 230 of the catheter 220 has a smaller bore that opens out proximally along the shaft of the catheter to the full cross section of the particular size being used. The smaller cross section of the tip may mean that a larger catheter can be used without insertion difficulties.

The tip portion 228 includes a drainage aperture 232 which is in fluid communication with the drainage bore 224 and an inflation aperture 234 which is in fluid communication with the inflation bore 226. In this embodiment the inflation aperture 234 is on an opposite side of the tip portion 228 from the drainage aperture 232. In this example the drainage aperture 232 is elongate having a first end 238 nearer the distal end 230 of the catheter 220 and a second end 240 furthest from the distal end 230.

An inflatable retention balloon 236 is attached to the tip portion 228 of the catheter 220. In a fully inflated state, as shown in FIGS. 3 to 5, the balloon 236 is substantially spherical, however, in other embodiments the balloon 236 may be of any suitable shape. The dimensions of the balloon 236 are such that the balloon fully surrounds the distal end 230 of the catheter 220. The balloon 236 extends along the tip portion 228 to a point on an opposite side of the drainage aperture 232 to the distal end 230. Preferably the balloon 236 extends just beyond the second end 240 of the drainage aperture 232, such that the drainage aperture 232 is located close to the surface of the balloon 236.

The inflatable balloon 236 around the catheter tip means that there is a soft fluid-filled membrane against the bladder wall when it collapses.

A surface of the balloon 236 includes a depression 242 that provides a passageway or recess in fluid communication with the drainage aperture 232. In preferred embodiments, the depression 242 in the surface of the balloon 236 does not extend beyond the distal end 230 of the tip portion 228. The depression 242 may be substantially in the shape of a spherical wedge or segment, and in preferred embodiments is substantially in the shape of half a spherical wedge.

The retention balloon 236, therefore, inflates to cover not only the tip but also all the circumference of the catheter 220 save the drainage aperture 232. This design resembles an orange with half a segment missing at the bottom where the drainage hole 232 is located. This ensures the bladder mucosa is kept away from the aperture 232 so it cannot get drawn in and damaged. The mucosa cannot collapse in on the aperture 232 like in a traditional catheter and so the risk of bladder damage is therefore minimised.

The location of the drainage aperture 232 nearer the tip or distal end 230 of the catheter 220 and surrounded by the balloon 236 makes the device less susceptible to kinking around the aperture 232 and therefore blocking. This means that the length of the aperture 232 can be increased compared with the traditional catheter which will allow for freer drainage of urine and less likelihood of blockage due to bladder debris or encrustation.

In preferred embodiments there is half the length of catheter 220 in the bladder (about 21 mm compared with about 42 mm) so less interference with normal biological bladder function.

As the drainage hole 232 is at the very base of the bladder it will not be able to collapse onto the hole. In any event the base of the bladder does not collapse down like the dome does.

FIG. 3 shows a 3D impression that illustrates both the shortened tip as well as the inflated balloon covering the tip. Just like in current catheters the inflated balloon will retain the catheter in the bladder but, as the drainage aperture is in the lower half of a segment without the balloon, it will allow complete bladder emptying. FIG. 4 (a front elevation) and FIG. 5 (a side elevation) show how the inflation tube links to the balloon and opens out into the balloon behind the urine drainage tube. The drawing also shows how the drainage aperture links to the drainage tube down the body of the catheter.

FIGS. 6 and 7 illustrate the cross sections of both an existing catheter design (FIG. 6) and the catheter of the present invention (FIG. 7). Catheters are supplied according to their external diameters and the narrower tip of the catheter of the present invention makes insertion of a particular sized catheter easier. Furthermore the length of the urine drainage aperture is longer in the catheter of the present invention (FIG. 7) compared to a traditional catheter (FIG. 6) which makes blockage less likely. As the drainage aperture of the catheter of the present invention is both nearer the distal end and surrounded by the balloon, it can safely be lengthened without risk of kinking. The traditional catheter balloon is well below the urine aperture leaving a significant length of soft tubing that is susceptible to kinking if the length of the aperture is too long.

A larger drainage hole will facilitate the efficient and complete emptying of the bladder and the graduated/tapered design allows easier insertion for a particular catheter size because of the graduated increase in cross-sectional area.

Figure 9:
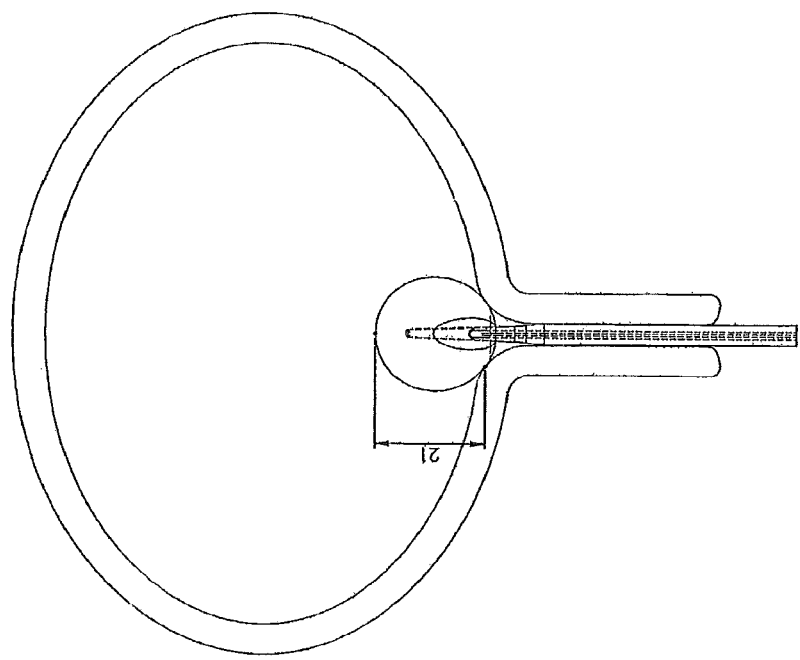
FIG. 9 shows an embodiment of a catheter according to the present invention in position within a bladder.
Figure 8:
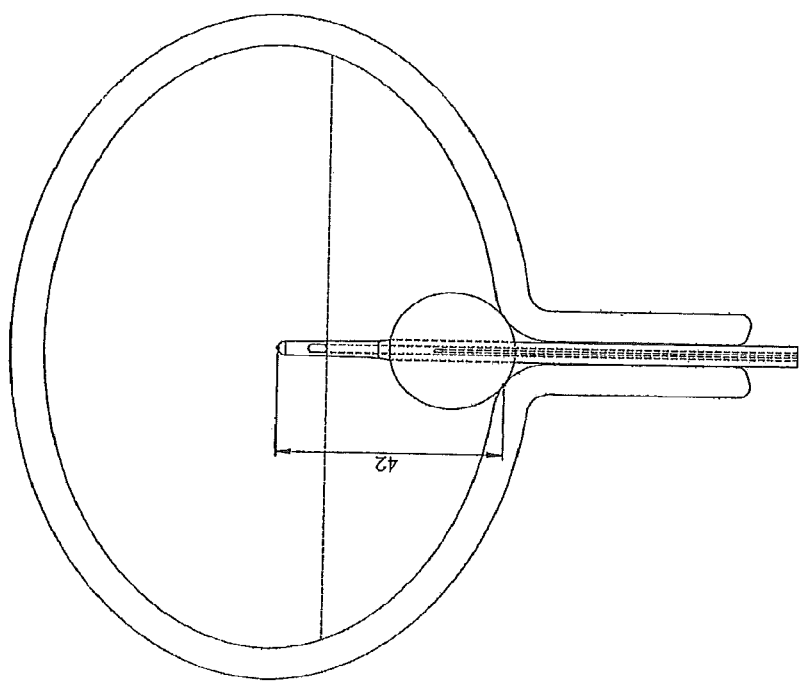
FIG. 8 shows an example of a know, prior art catheter in position within a bladder.

FIGS. 8 and 9 show the traditional catheter and catheter of the present invention for a side by side comparison in the bladder so all the differences can be appreciated. The analogy with a bath or sink helps to make the changes understandable. The traditional catheter (FIG. 8) always allows a significant volume of urine to be retained in the bladder which is the major contributor to the consequence of frequent blockage. Excess urine drains via the 'overflow' so the bladder cannot fill above the drainage hole unless the outflow tubing blocks but crucially neither can it empty. The catheter of the present invention (FIG. 9) allows complete drainage down the 'plughole' so urine cannot fester in the bladder and cause these well recognised problems. The retention balloon is perfectly adequate for retaining the catheter in the bladder and looks like an orange with half a segment missing at the bottom where the drainage aperture is located. The catheter of the present invention allows both for a soft fluid membrane to be the catheter tip and also for a shorter length of catheter to be within the bladder which should both dramatically reduce the risk of bladder wall damage.

What is claimed is:

1. A catheter comprising:
    an elongate shaft having a longitudinal drainage bore for conveying fluid along the shaft;
    an elongate tip portion extending from an end of the shaft, the tip portion having a distal end furthest from the shaft;
    a drainage aperture provided in the tip portion, said aperture being in fluid communication with said bore; and
    an inflatable balloon element attached to said tip portion, the balloon element being configured such that, when inflated, a wall of the balloon element extending over the tip portion is spaced from the distal end of the tip portion and the balloon element extends around the circumference of the catheter save the drainage aperture and extends to a point on a side of the drainage aperture opposite to the distal end of the tip portion, a surface of the balloon element defining a depression providing a passageway in fluid communication with the drainage aperture;
    wherein the drainage aperture is located at a bottom of the balloon element.

2. A catheter as claimed in claim 1 further comprising:
    an inflation bore provided in the shaft; and
    an inflation aperture provided in the tip portion, the inflation aperture being in fluid communication with the inflation bore and with an internal volume of the balloon element.

3. A catheter as claimed in claim 2, wherein the inflation aperture is provided on an opposite side of the tip portion to the drainage aperture.

4. A catheter as claimed in claim 1, wherein a dimension of the balloon element, when inflated, in a longitudinal direction is at least three times the dimension of the drainage aperture in the longitudinal direction.

5. A catheter as claimed in claim 1, wherein the tip portion is tapered.

6. A catheter as claimed in claim 1, wherein a length of the tip portion between the drainage aperture and the distal end is at least two times the length of the drainage aperture in the longitudinal direction.

7. A catheter as claimed in claim 1, wherein the balloon element, when inflated, extends to a point that is on an opposite side of the drainage aperture from the distal end of the tip portion.

8. A catheter as claimed in claim 1, wherein, when the balloon element is inflated, the depression in the surface of the balloon element does not extend beyond the distal end of the tip portion.

9. A catheter as claimed in claim 1, wherein the balloon element, when inflated, is substantially spherical.

10. A catheter as claimed in claim 1, wherein the balloon element is configured such that when fully inflated the balloon element is spaced from the distal end of the tip portion.

* * * * *